US00PP25466P3

(12) United States Plant Patent
McGranahan et al.

(10) Patent No.: US PP25,466 P3
(45) Date of Patent: Apr. 28, 2015

(54) WALNUT TREE NAMED 'SOLANO'

(50) Latin Name: *Juglans regia*
Varietal Denomination: Solano

(71) Applicant: The Regents of the University of California, Oakland, CA (US)

(72) Inventors: Gale McGranahan, Davis, CA (US); Charles Leslie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 189 days.

(21) Appl. No.: 13/694,337

(22) Filed: Nov. 20, 2012

(65) Prior Publication Data

US 2014/0143919 P1 May 22, 2014

(51) Int. Cl.
*A01H 5/00* (2006.01)

(52) U.S. Cl.
USPC ..... Plt./154

(58) Field of Classification Search
CPC ..... A01H 5/0825; A01H 5/08; A01H 5/00
USPC ..... Plt./154
See application file for complete search history.

(56) References Cited

PUBLICATIONS

The Mar. 1, 2003 Test Agreement For Trees (No. 2004-5010) between David Scheuring and The Regents Of The University of California, 8 pages.
The Feb. 1, 2008 Test Agreement For Trees (No. 2008-5004) between FDS Farms and The Regents Of The University of California, 6 pages.
The Feb. 1, 2010 Test Agreement For Trees (No. 2010-5002) between Carriere & Sons and The Regents Of The University of California, 7 pages.
The Mar. 1, 2010 Test Agreement For Trees (No. 2010-5007) between Sierra Gold Nurseries, Inc. and The Regents Of The University of California, 7 pages.
The Feb. 1, 2010 Test Agreement For Trees (No. 2010-5013) between The Burchell Nursery, Inc. and The Regents Of The University of California, 6 pages.
The Jan. 1, 2010 Test Agreement For Trees (No. 2010-5014) between Golden Valley Nursery and The Regents Of The University of California, 7 pages.
The Mar. 1, 2008 Test Agreement For Trees (No. 2011-5023) between Golden Valley Farms, Inc. and The Regents Of The University of California, 7 pages.
The Feb. 1, 2011 Test Agreement For Trees (No. 2011-5027) between Jerry K. Moore, Inc. and The Regents Of The University of California, 7 pages.
The Feb. 1, 2012 Test Agreement For Trees (No. 2012-5002) between Green Tree Nursery and The Regents Of The University of California, 7 pages.
The Feb. 1, 2012 Test Agreement For Trees (No. 2012-5003) between Dave Wilson Nursery, Inc. and The Regents Of The University of California, 7 pages.
The Feb. 1, 2012 Test Agreement For Trees (No. 2012-5004) between Martinez Orchards, Inc. and The Regents Of The University of California, 7 pages.
The Feb. 1, 2012 Test Agreement For Trees (No. 2012-5005) between Stuke Nursery Co., Inc. and The Regents Of The University of California, 7 pages.
The Feb. 1, 2012 Test Agreement For Trees (No. 2012-5007) between Cal-Western Nurseries and The Regents Of The University of California, 7 pages.
The Feb. 1, 2012 Test Agreement For Trees (No. 2012-5008) between Bert Crane Orchards, L.P. and The Regents Of The University of California, 6 pages.
The Mar. 1, 2012 Test Agreement For Trees (No. 2012-5010) between Bear River Walnut Ranch and The Regents Of The University of California, 7 pages.

*Primary Examiner* — June Hwu
(74) *Attorney, Agent, or Firm* — Morrison & Foerster LLP

(57) ABSTRACT

A new and distinct cultivar of walnut tree denominated 'Solano' is described. This new cultivar, 'Solano', comes into bearing young, with an excellent yield. 'Solano' forms jumbo-sized walnuts that possess light-colored kernels with little size variation in a given harvest. 'Solano' bears fruit terminally and laterally and yields a crop that can be harvested approximately 2 weeks before 'Chandler' (U.S. Plant Pat. No. 4,388). 'Solano' is also protandrous, bearing male flowers before female flowers.

10 Drawing Sheets

Latin name: Botanical/commercial classification: (*Juglans regia*), new English walnut tree cultivar.

Varietal denomination: The varietal denomination of the claimed walnut is 'Solano'.

BACKGROUND OF INVENTION

The present invention relates to a new and distinct cultivar of walnut tree (*Juglans regia*) that has been denominated as 'Solano' and more particularly to a walnut tree that has a harvest date approximately 2 weeks earlier than the walnut tree cultivar 'Chandler' (U.S. Plant Pat. No. 4,388), and that further produces a walnut that is jumbo in size with light colored kernels.

It has long been recognized as desirable to provide walnut trees bearing large crops that are ripe for commercial harvesting and shipment early in the harvest season. The tree of the present cultivar, 'Solano', produces a nut that has a quality similar to the highest quality cultivar 'Chandler' (U.S. Plant Pat. No. 4,388). However, the new cultivar is ready for harvest approximately 2 weeks before 'Chandler', which is about the same time as the reference cultivar 'Vina' (old cultivar; not patented).

The new *Juglans regia* walnut tree of the present invention was created at Davis, Calif. in Year 1 by a controlled pollination between the cultivar 'Chico' and 'UC67-13' (neither patented). The pedigree is illustrated (FIG. 1).

Seeds from the cross were planted and the resulting 29 trees were carefully observed along with other trees in the walnut breeding program. When the trees began to bear nuts, data were collected annually on leafing date, first, peak and last female flower bloom, first, peak and last male bloom, blight severity, and yield (Table 1). Nuts were sampled, cracked, and data was collected on shell appearance, shell thickness, shell integrity, shell strength, nut weight, kernel weight, percent kernel, ease of kernel removal, kernel color, and percent kernel shrivel (Table 1). A single tree was selected from among progeny of this controlled cross based on its superior attributes. This selection was originally designated 'UC95-11-16' and is now designated as the 'Solano' cultivar after the county in California. Compared to 'Solano', the parent 'UC67-13' has larger nuts, an earlier harvesting date, and is susceptible to pistillate flower abscission. The parent 'Chico' is protogynous and has smaller nuts than 'Solano' with a more difficult to extract kernel (Table 1).

The new 'Solano' cultivar of the present invention has been asexually reproduced by grafting at Davis, Calif. and in various field trials on 'Paradox' rootstock. The distinctive characteristics of the new cultivar have been found to be stable and are transmitted to the new trees when asexually propagated.

SUMMARY OF THE INVENTION

It was found that the walnut cultivar 'Solano' of the present invention exhibits the following combination of characteristics:

a) comes into bearing young, with an excellent yield;
b) forms jumbo-sized walnuts that possess light-colored kernels with little size variation in a given harvest;
c) bears fruit terminally and laterally;
d) yields a crop that can be harvested approximately 2 weeks before 'Chandler' (U.S. Plant Pat. No. 4,388); and
e) is protandrous, bearing male flowers before female flowers.

BRIEF DESCRIPTION OF THE TABLE

Table 1 shows tree and nut evaluations for both parents and the most common walnut cultivar 'Chandler'.

BOTANICAL DESCRIPTION OF THE PLANT

The following description is based on an ungrafted walnut tree on its own roots and trees subsequently grafted on 'Paradox' rootstock in selection blocks at Davis, Calif., Chico, Calif., and Parlier, Calif.; as well as in grower trials near Madison, Calif., near Durham, Calif., and near Wheatland, Calif. The first data were collected on the own rooted tree from Year 4 at age 3 years, to Year 11, age 10. Data from Year 9 to Year 15 were collected from grafted trees.

The Munsell Color Charts for Plant Tissues (GretagMacbeth LLC, 617 Little Britain Road, New Windsor, N.Y. 12553-6148) was used in the identification of color. Also, common color terms are to be accorded their ordinary dictionary significance.

Botanical classification: *Juglans regia.*

*Female parent.*—'UC67-13'.

Figure 1:
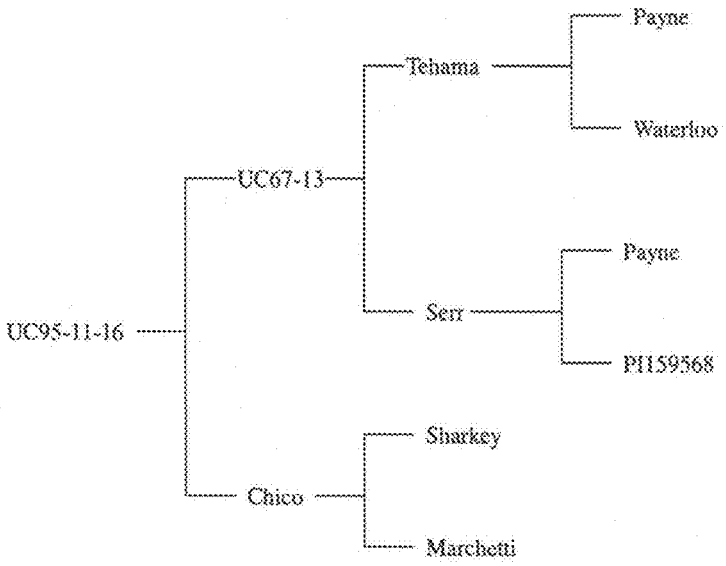
FIG. 1 shows pedigree of the 'Solano' walnut tree.

*Male parent.*—'Chico'. The pedigree is shown in FIG. 1.

Figure 2:
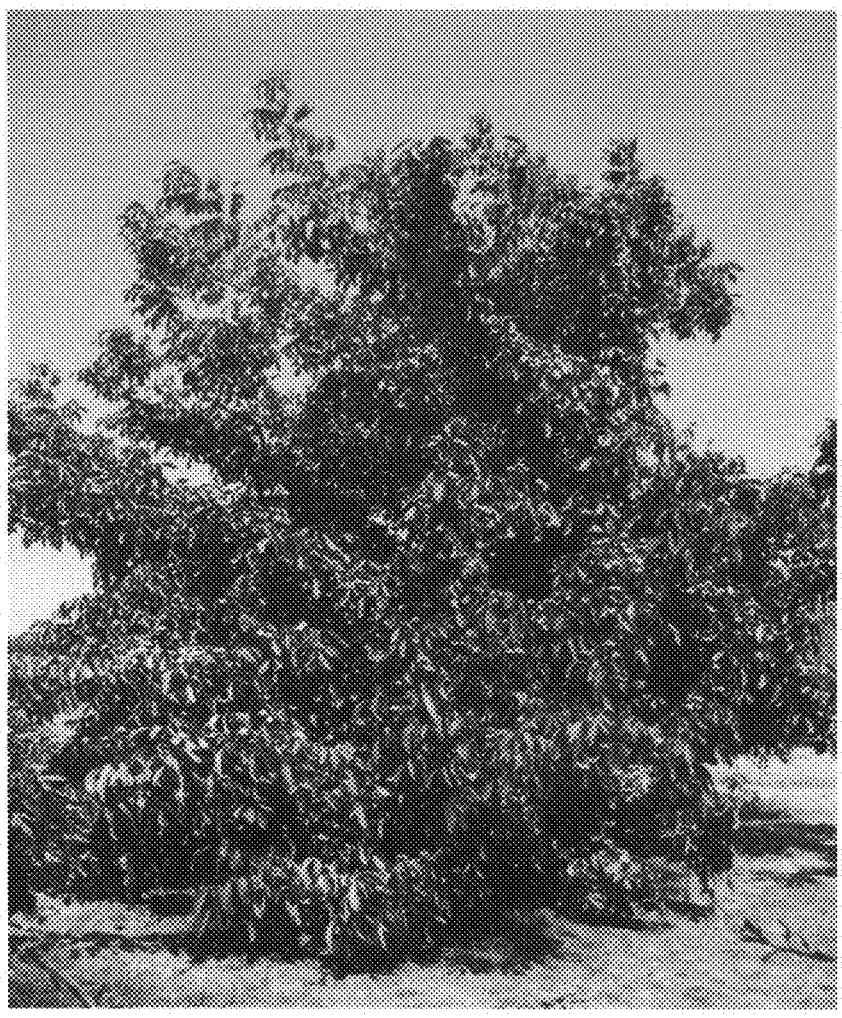
FIG. 2 shows a 'Solano' walnut tree at 8 years old.
Figure 3:
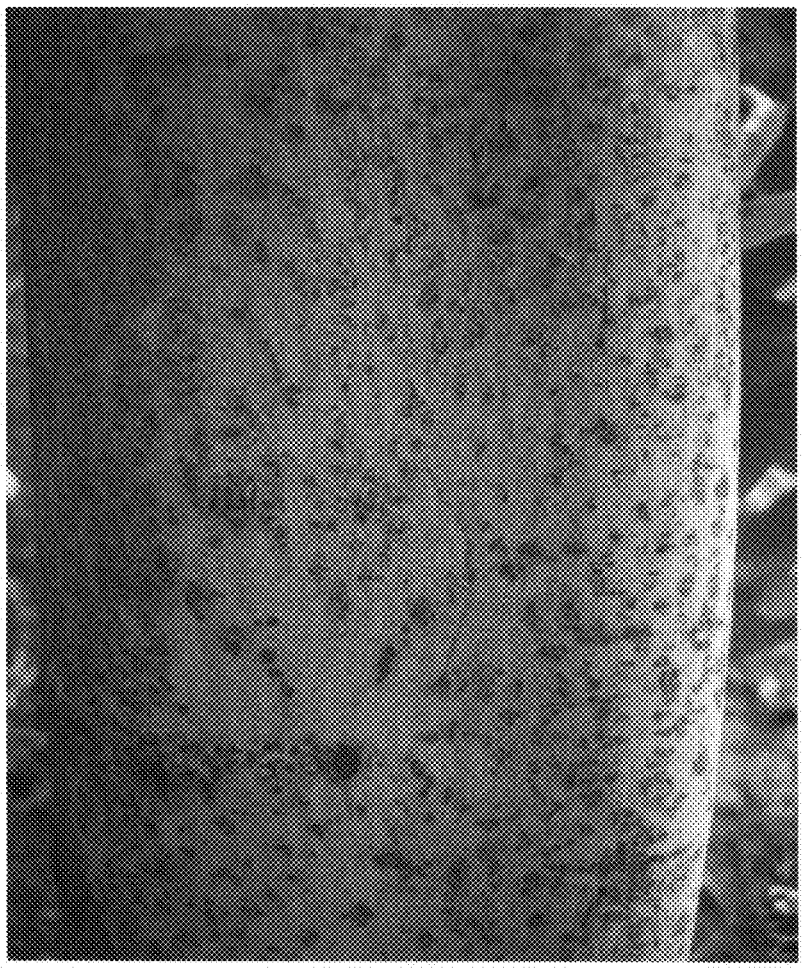
FIG. 3 shows bark of a 'Solano' walnut tree.

Plant: The growth habit of the plant is illustrated in FIG. 2. This 8 year old tree is approximately 7.2 meters in height with a canopy diameter of 8.1 meters. The trunk diameter at 0.5 meters above the ground is approximately 24 cm. The silvery grey bark is typical of *Juglans regia*. The young bark is brown (5Y 5/2) and the older bark is grey (5Y 7.5/2) with raised lighter lenticels (2.5Y 8/2) (FIG. 3). The texture of the trunk is smooth, as is typical of *Juglans regia*. Lenticels are round to oval in shape, 1-10 mm×1-3 mm in size. 'Solano' has vigor similar to 'Chandler'.

Figure 4:
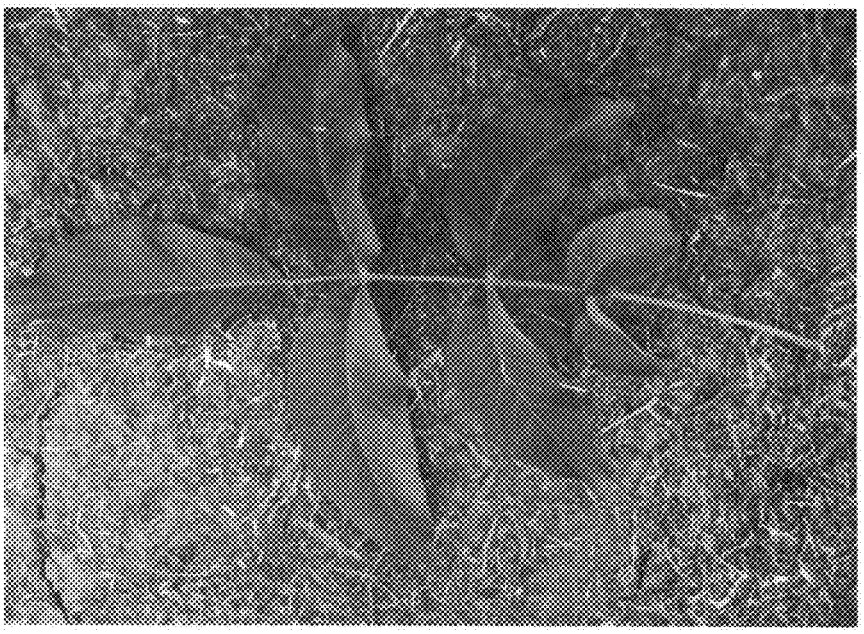
FIG. 4 shows an adaxial view of a typical leaf of a 'Solano' walnut tree.
Figure 5:
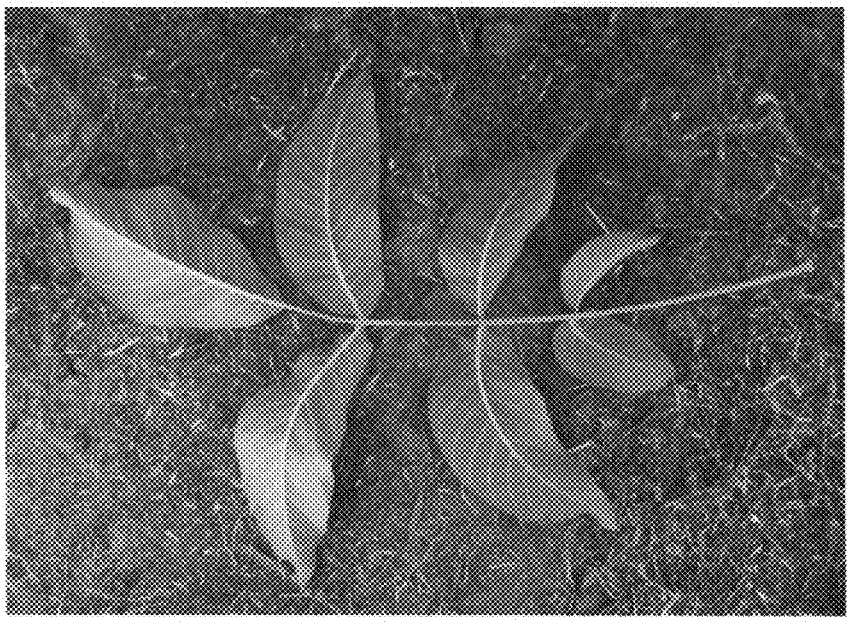
FIG. 5 shows an abaxial view of a typical leaf of a 'Solano' walnut tree.

Foliage: The dark green foliage is illustrated in FIG. 4 and FIG. 5, and is typical of *Juglans regia*. Leafing out date between Year 4 and Year 15 has occurred on March 25$^{th}$ on the average. For comparative purposes the 'Chandler' cultivar leaf-out is April 4$^{th}$. Leaf fall normally occurs in late November, which is typical of *Juglans regia*, but can vary considerably depending on fall weather and timing of the first frost. The typical leaf coloration is green (adaxial SGY 3/4, abaxial SGY 5/4). The leaves are pinnately compound with 7-9 leaflets. The full leaf length is approximately 38 cm and the width is 30 cm. Leaflets are broadly elliptical and entire. The leaflet has a smooth texture with an apex shape that is smooth and a base shape that is sloped. The terminal leaflet averages 17 cm in length and 9 cm in width. The middle leaflets average 15 cm in length and 6 cm in width, and the proximal leaflets average 6 cm in length and 3.5 cm in width. The rachis averages 22 cm in length and 2-4 mm in diameter. The rachis is not persistent. Petiole length is 7 cm and is 2.5GY 7/6 in color.

Inflorescence: The tree is precocious with excellent yield being noted at age 3 years. Male flowers (catkins) were first present at age 4 years. This delay in male maturity is typical of *Juglans regia*. The average number of catkins is one catkin per inflorescence. From Year 4 to Year 15, average first female bloom occurred on April 9$^{th}$, peak bloom on April 13$^{th}$ and last bloom on April 19$^{th}$. From Year 5 to Year 15, average male flowering (pollen shedding) began March 28$^{th}$, peaked on April 2$^{nd}$, and terminated on April 11$^{th}$. Pollen shedding in this protandrous cultivar does not completely cover pistillate bloom, suggesting that a pollenizer would be needed for maximum yield in isolated areas. 'Chandler' (U.S. Plant Pat. No. 4,388), 'Howard' (U.S. Plant Pat. No. 4,405), and 'Tulare' (U.S. Plant Pat. No.

Figure 6:
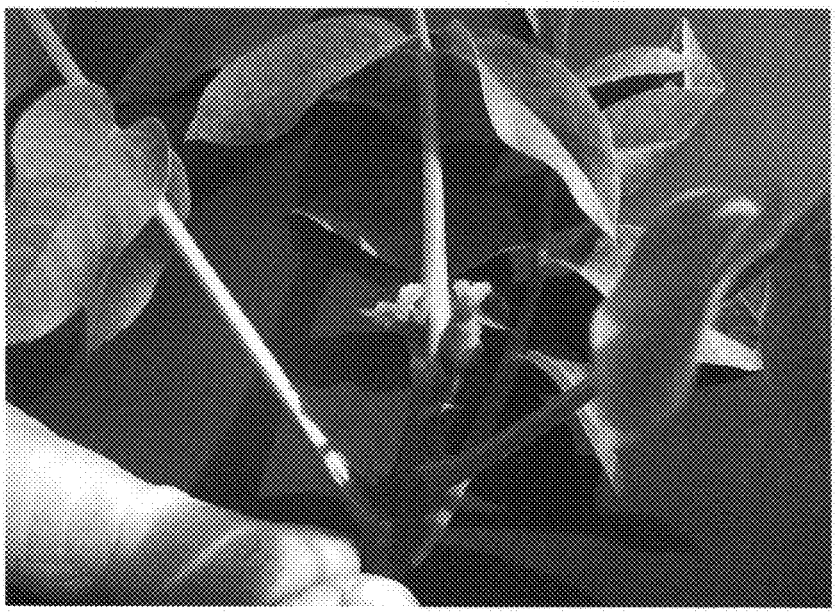
FIG. 6 shows female flowers of a 'Solano' walnut tree.
Figure 7:
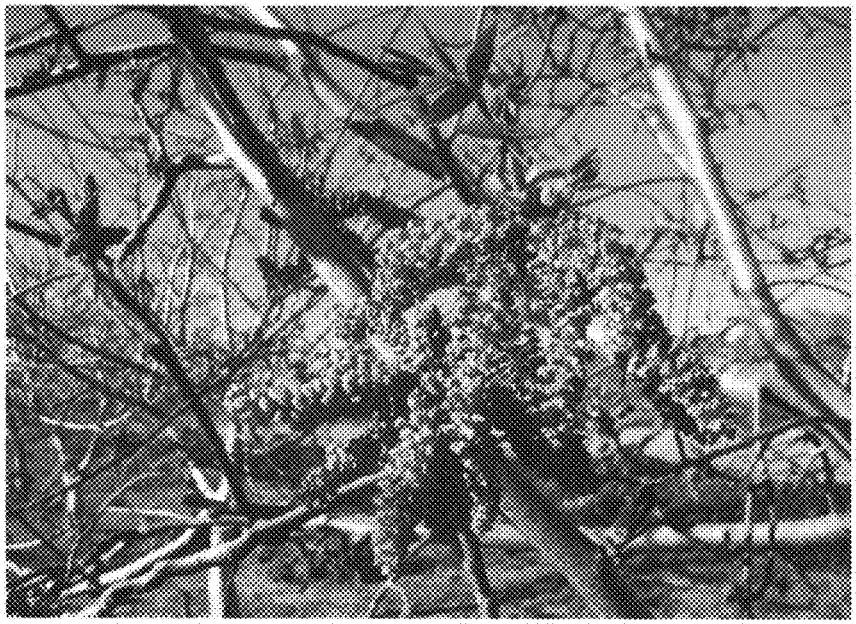
FIG. 7 shows catkins (male flowers) of a 'Solano' walnut tree.

8,268), would all be satisfactory pollenizers. The female flowers are typical of *Juglans regia* (FIG. 6), with 2-3 flowers per inflorescence borne on 1 cm spike at both terminal and lateral positions on current season's growth. Approximately 100% of the lateral buds contain inflorescences making yields much greater than trees that only bear flowers terminally. A typical female flower is approximately 5 to 7 mm at anthesis and floral organs are typical of *Juglans regia*. The flowers appear vase-shaped when the 2 plumose stigmatic arms are curved outward. There are no petals. The female flowers are green in color (5GY 7/8). The flower fragrance is typical of *Juglans regia* and is not noticeably different than the foliage fragrance. The male flowers (FIG. 7) are borne on catkins, between 7.5 and 14 cm in length and 1.5 cm in diameter, and are green in color (5GY 7/8).

Figure 8:
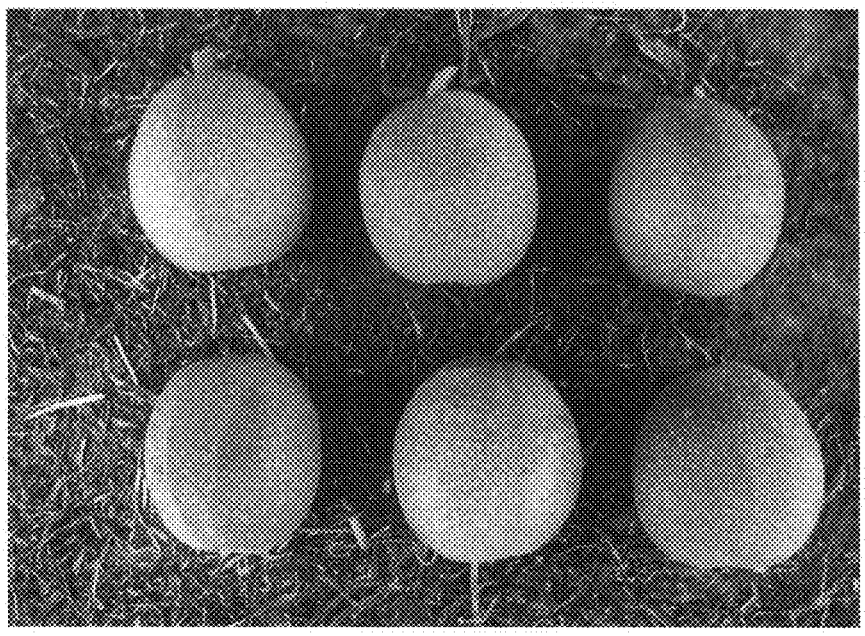
FIG. 8 shows hulls from a 'Solano' walnut tree before opening and exposing the nuts.
Figure 9:
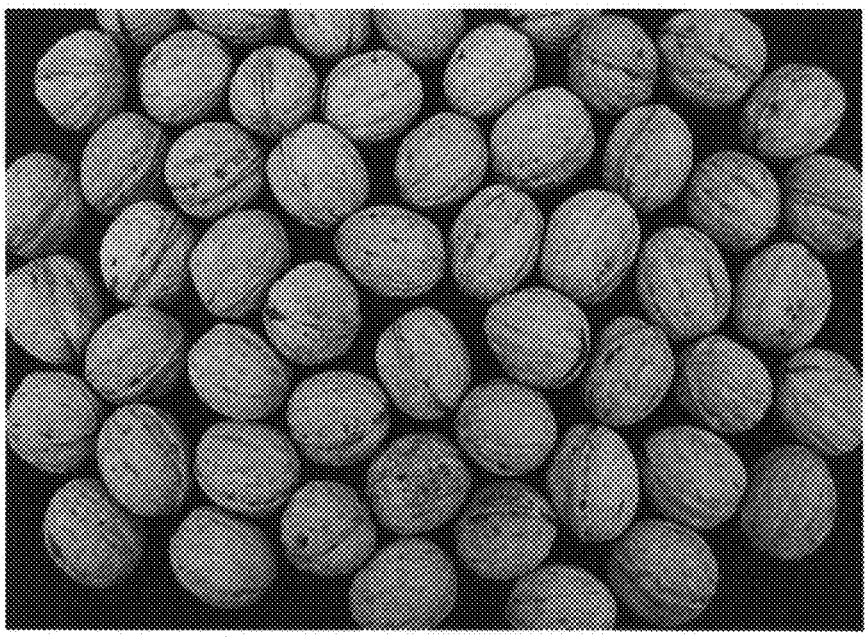
FIG. 9 shows nuts from a 'Solano' walnut tree.
Figure 10:
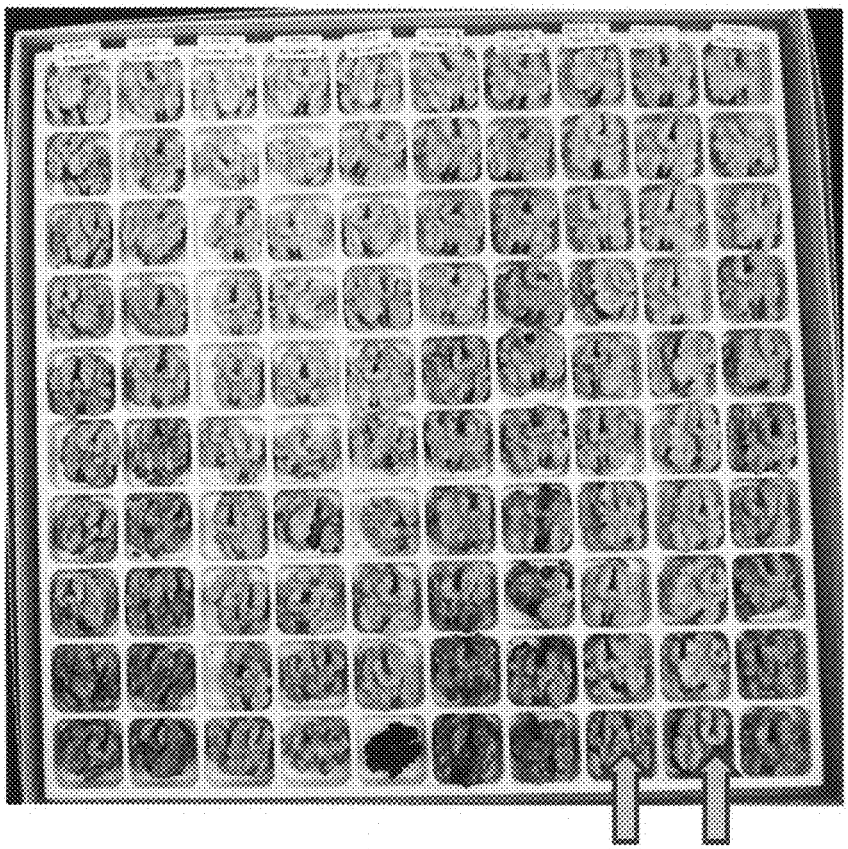
FIG. 10 shows kernels from a 'Solano' walnut tree.

Walnuts: The new cultivar 'Solano' commonly harvests about 2 weeks before 'Chandler', about one week after 'Payne', and is similar in timing to 'Vina'. The new cultivar has excellent yields of mostly jumbo-sized walnuts. The hull is globose, 5.5 cm×5.0 cm, 6 mm thick, and 2.5GY 6/6 in color with numerous lighter speckles (FIG. 8). The hull is not persistent. The nut has a shape that is base rounded in shape and an apex that is moderately pointed in shape. The nut is broadly elliptical, slightly rough but uniform and attractive appearance, is tan in color (7.5YR 6/4), and measures approximately 42 mm in length and 36 mm in width (FIG. 9). The shell is 1.3 mm thick, relatively strong and well-sealed, suitable for in-shell marketing, and the kernel is easy to remove. The nut has a primary dividing membrane that is 0.2 mm thick. The nut lacks a secondary dividing membrane. The kernel has an average length of 3.45 cm and an average width of 3.06 cm. The kernel weight averages 8.0 g and makes up 55% of the total nut weight of 14.6 g. Kernel color is considered excellent (FIG. 10), and scores mostly in the light to extra light categories (i.e.; 33.8% extra light, 57.4% light, 9.8% light amber, and 0% amber) of the USDA Standards for Grades of Shelled Walnuts as determined by using the standard Walnut Color Chart for kernels published by the Dried Fruit Association of California. FIG. 10 provides a comparison of the kernels of the new 'Solano' cultivar (95-011-16) to other walnut cultivars (the kernels of 'Solano' are shown in the two columns indicated by the arrows). In addition, kernels of 'Solano' have averaged 54.8 on the Relative Light Index used by Diamond Foods of Stockton, Calif. Walnuts of the new cultivar 'Solano' are typical of commercial walnuts in terms of flavor and firmness, the latter varying according to the percent moisture after drying. Walnuts of the new cultivar 'Solano' exhibit storage and shipping quality that is typical of *Juglans regia*.

Disease susceptibility: The response of the new cultivar 'Solano' to *Xanthomonas campestris* pv. *juglandis* and walnut husk fly (*Rhagoletis completa*) appears to be typical of mid-season cultivars.

Usage: The new cultivar 'Solano' of the present invention provides a relatively early to mid-season walnut with high quality light-colored kernels that can be used cracked or in-shell.

TABLE 1

Performance of 'Solano' compared to 'UC67-13', 'Chico', 'Chandler', and 'Vina'.

| Trait[1] | | Variety | | | | | |
|---|---|---|---|---|---|---|---|
| | | Solano[2] | | | UC67-13[3] | | |
| Leafing date | | 3/25 | (1.83) | 22[4] | 3/24 | (1.08) | 19 |
| Pollen shed date | First | 3/28 | (2.03) | 13 | 3/31 | (1.74) | 17 |
| | Peak | 4/2 | (1.98) | 13 | 4/6 | (1.52) | 17 |
| | Last | 4/11 | (1.82) | 13 | 4/19 | (1.33) | 16 |
| Female bloom date | First | 4/9 | (1.58) | 18 | 4/6 | (1.31) | 17 |
| | Peak | 4/13 | (1.50) | 18 | 4/12 | (1.15) | 16 |
| | Last | 4/19 | (1.67) | 18 | 4/19 | (1.14) | 16 |
| Harvest date | | 9/24 | (1.20) | 3.6 | 9/21 | (1.64) | 17 |
| Days after Payne leafing | | 7 | (1.05) | 19 | 6 | (1.43) | 11 |
| Days after Chandler leafing | | −9 | (0.91) | 19 | −12 | (1.19) | 11 |
| Catkin abundance | | 5.2 | (0.61) | 14 | 6.3 | (0.49) | 18 |
| Female abundance | | 6.3 | (0.22) | 16 | 5.8 | (0.35) | 11 |
| Flowers/Inflorescence | | 2.0 | (0) | 17 | 2.0 | (0) | 16 |
| Percent lateral bud fruitfulness | | 95.3 | (2.29) | 17 | 96.6 | (1.18) | 16 |
| Yield | | 6.4 | (0.18) | 32 | 5.6 | (0.31) | 17 |
| Shell | Texture | 4.9 | (0.07) | 35 | 5.0 | (0.67) | 10 |
| | Color | 4.7 | (0.10) | 35 | 4.8 | (0.42) | 10 |
| | Seal | 5.1 | (0.06) | 35 | 5.0 | (0) | 11 |
| | Strength | 5.0 | (0.06) | 35 | 5.1 | (0.30) | 11 |
| | Integrity | 7.0 | (0) | 35 | 7.0 | (0) | 5 |
| | Thickness | 1.3 | (0.02) | 35 | 1.5 | (0.13) | 11 |
| | Packing tissue | 5.0 | (0) | 35 | 5.1 | (0.57) | 10 |
| Kernel | Inshell weight | 14.6 | (0.24) | 35 | 15.3 | (1.78) | 11 |
| | Kernel weight | 8.0 | (0.16) | 35 | 8.5 | (1.55) | 11 |
| | Percent kernel | 54.6 | (0.45) | 35 | 55.4 | (2.16) | 11 |
| | Fill | 5.4 | (0.09) | 35 | 4.7 | (1.27) | 11 |
| | Plumpness | 5.4 | (0.08) | 35 | 4.7 | (1.10) | 11 |
| | Ease of removal | 4.7 | (0.07) | 35 | 4.3 | (0.48) | 10 |
| | Percent blank | 0.6 | (0.40) | 35 | 2.7 | (6.47) | 4 |
| | Percent extra light | 33.8 | (5.48) | 35 | 18.8 | (35.7) | 11 |
| | Percent light | 57.4 | (4.92) | 35 | 72.6 | (33.7) | 11 |
| | Percent light amber | 9.8 | (2.34) | 35 | 6.7 | (4.05) | 11 |
| | Percent amber | 0 | 0 | 35 | 1.8 | (6.03) | 11 |
| | Percent tip shrivel | 11.8 | (3.2) | 35 | 1.1 | (3.51) | 10 |
| | Percent veins | 16.6 | (3.12) | 35 | 44.4 | (22.4) | 11 |

| Trait[1] | | Variety | | | | | |
|---|---|---|---|---|---|---|---|
| | | Chico[3] | | | Chandler[3] | | |
| Leafing date | | 3/22 | (1.13) | 27 | 4/4 | (0.72) | 80 |
| Pollen shed date | First | 4/7 | (1.30) | 23 | 4/6 | (0.83) | 75 |
| | Peak | 4/13 | (1.16) | 24 | 4/14 | (0.72) | 74 |
| | Last | 4/20 | (1.01) | 23 | 4/21 | (0.81) | 73 |
| Female bloom date | First | 3/25 | (0.92) | 25 | 4/17 | (0.72) | 77 |
| | Peak | 4/1 | (1.02) | 25 | 4/23 | (0.68) | 77 |
| | Last | 4/9 | (1.15) | 25 | 4/30 | (0.71) | 76 |
| Harvest date | | 9/18 | (1.76) | 24 | 10/8 | (0.72) | 91 |
| Days after Payne leafing | | 3 | (0.45) | 18 | 17 | (0.60) | 64 |
| Days after Chandler leafing | | −15 | (0.97) | 18 | 0 | (0.34) | 64 |
| Catkin abundance | | 5.3 | (0.28) | 23 | 4.9 | (0.20) | 75 |
| Female abundance | | 6.1 | (0.26) | 22 | 6.1 | (0.13) | 67 |
| Flowers/Inflorescence | | 2.0 | (0) | 25 | 2.0 | (0.01) | 70 |
| Percent lateral bud fruitfulness | | 99.9 | (0.08) | 25 | 95.7 | (0.75) | 68 |

TABLE 1-continued

Performance of 'Solano' compared to 'UC67-13', 'Chico', 'Chandler', and 'Vina'.

| | | | | | | | |
|---|---|---|---|---|---|---|---|
| Yield | | 6.3 | (0.26) | 27 | 5.7 | (0.12) | 92 |
| Shell | Texture | 4.2 | (0.15) | 17 | 4.7 | (0.05) | 87 |
| | Color | 4.6 | (0.15) | 17 | 4.3 | (0.06) | 87 |
| | Seal | 5.4 | (0.15) | 18 | 4.9 | (0.03) | 88 |
| | Strength | 5.7 | (0.11) | 18 | 4.5 | (0.07) | 88 |
| | Integrity | 7.1 | (0.10) | 14 | 7.0 | (0) | 82 |
| | Thickness | 1.5 | (0.03) | 18 | 1.3 | (0.02) | 88 |
| | Packing tissue | 5.6 | (0.12) | 17 | 4.7 | (0.05) | 86 |
| Kernel | Inshell weight | 11.4 | (0.29) | 18 | 13.4 | (0.19) | 88 |
| | Kernel weight | 5.3 | (0.12) | 18 | 6.6 | (0.10) | 88 |
| | Percent kernel | 47.1 | (0.57) | 18 | 49.5 | (0.27) | 88 |
| | Fill | 5.7 | (0.47) | 18 | 4.5 | (0.06) | 88 |
| | Plumpness | 4.5 | (0.20) | 18 | 4.3 | (0.06) | 87 |
| | Ease of removal | 6.5 | (0.17 | 17 | 3.9 | (0.05) | 87 |
| | Percent blank | 2.4 | (1.06) | 17 | 1.3 | (0.36) | 87 |
| | Percent extra light | 9.4 | (5.60) | 17 | 50.8 | (4.22) | 86 |
| | Percent light | 76.0 | (7.41) | 17 | 44.2 | (3.82) | 86 |
| | Percent light amber | 12.0 | (4.81) | 17 | 4.6 | (1.32) | 86 |
| | Percent amber | 2.6 | (2.03) | 17 | 0.4 | (0.21) | 86 |
| | Percent tip shrivel | 0 | (0) | 17 | 30.5 | (2.60) | 86 |
| | Percent veins | 19.2 | (5.48) | 17 | 18.3 | (2.78) | 85 |

| Trait[1] | | | Variety Vina[3] | | |
|---|---|---|---|---|---|
| Leafing date | | | 3/26 | (0.89) | 41 |
| Pollen shed date | | First | 3/28 | (0.99) | 39 |
| | | Peak | 4/5 | (1.01) | 39 |
| | | Last | 4/14 | (1.04) | 39 |
| Female bloom date | | First | 4/8 | (1.05) | 40 |
| | | Peak | 4/13 | (0.87) | 40 |
| | | Last | 4/21 | (0.93) | 40 |
| Harvest date | | | 9/23 | (1.06) | 49 |
| Days after Payne leafing | | | 8 | (0.47) | 39 |
| Days after Chandler leafing | | | −9 | (0.62) | 39 |
| Catkin abundance | | | 5.7 | (0.21) | 39 |
| Female abundance | | | 6.6 | (0.16) | 35 |
| Flowers/Inflorescence | | | 2.0 | (0) | 37 |
| Percent lateral bud fruitfulness | | | 93.4 | (1.92) | 34 |
| Yield | | | 6.5 | (0.14) | 51 |
| Shell | Texture | | 5.0 | (0) | 49 |
| | Color | | 5.2 | (0.07) | 49 |
| | Seal | | 5.2 | (0.05) | 50 |
| | Strength | | 5.1 | (0.04) | 50 |
| | Integrity | | 7.0 | (0) | 46 |
| | Thickness | | 1.4 | (0.02) | 50 |
| | Packing tissue | | 5 | (0.03) | 49 |
| Kernel | Inshell weight | | 12.8 | (0.24) | 50 |
| | Kernel weight | | 3.3 | (0.13) | 50 |
| | Percent kernel | | 49.3 | (0.30) | 50 |
| | Fill | | 5.1 | (0.08) | 50 |
| | Plumpness | | 4.8 | (0.08) | 50 |
| | Ease of removal | | 4.9 | (0.11) | 50 |
| | Percent blank | | 2.0 | (0.58) | 49 |
| | Percent extra light | | 4.1 | (2.90) | 49 |
| | Percent light | | 48.1 | (4.99) | 49 |
| | Percent light amber | | 45.1 | (4.86) | 49 |

TABLE 1-continued

Performance of 'Solano' compared to 'UC67-13', 'Chico', 'Chandler', and 'Vina'.

| | | | | |
|---|---|---|---|---|
| | Percent amber | 2.5 | (1.33) | 49 |
| | Percent tip shrivel | 2.3 | (0.91) | 49 |
| | Percent veins | 30.4 | (5.04) | 49 |

[1]See attached key for description of scores;
[2]Data Year 4 to Year 15;
[3]Data Year Minus 6 to Year 15;
[4]Data mean, (Std. Error), n In Table 1 the data for 'Solano' was collected over 11 years, from Year 4 to Year 15. The data for 'UC67-13', 'Chico', 'Chandler', and 'Vina' was collected over the course of 21 years, from Year Minus 6 to Year 15. Shell color in Table 1 is a comparison as scored for breeding evaluations on a 1-9 scale for relative shell color, where a score of 3 is light, 5 is medium and 7 is dark. In Table 1, in the row "Days after Chandler leafing" negative numbers refer to days before 'Chandler' leafing. Additionally, in footnote 4 of Table 1, "n" refers to the number of observations. Accordingly, the data in Table 1 are listed as mean values of the number of observations, including the standard error (Std. Error) in parentheses.

KEY FOR TABLE 1

| | |
|---|---|
| Tree evaluation | |
| Catkin abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Nut and kernel traits | |
| Texture | Shell texture: 3, smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial areas of shell missing; 5 small areas of shell missing; 6 hole in stem end; 7 complete shell |
| Thickness | Shell thickness at mid-cheek in mm |
| Packing tissue | Inner lining: 3 thin; 5 medium; 7 thick |
| Inshell weight | g |
| Kernel weight | g |
| Kernel % | Kernel wt/ inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like 'Chandler' |
| Veins % | Percent of kernels with conspicuous veins |

"DFA" refers to Dried Fruit Association of California

What we claim is:

1. A new and distinct cultivar of walnut tree designated 'Solano' as shown and described herein.

* * * * *